United States Patent
Hardcastle, III

(10) Patent No.: US 7,318,672 B2
(45) Date of Patent: Jan. 15, 2008

(54) SPECIMEN HEATER AND CONTROL SYSTEM FOR ACCELERATED WEATHERING TEST APPARATUS

(75) Inventor: Henry K. Hardcastle, III, Phoenix, AZ (US)

(73) Assignee: Atlas Material Testing Technology, L.L.C., Chicago, IL (US)

( * ) Notice: Subject to any disclaimer, the term of this patent is extended or adjusted under 35 U.S.C. 154(b) by 55 days.

(21) Appl. No.: 11/095,234

(22) Filed: Mar. 31, 2005

(65) Prior Publication Data

US 2006/0222046 A1 Oct. 5, 2006

(51) Int. Cl.
*G01N 17/00* (2006.01)

(52) U.S. Cl. .............. 374/109; 374/57; 356/51

(58) Field of Classification Search .......... 374/109, 374/57
See application file for complete search history.

(56) References Cited

U.S. PATENT DOCUMENTS

| | | | | |
|---|---|---|---|---|
| 2,523,322 | A * | 9/1950 | Ornstein et al. ............... 374/57 |
| 3,500,682 | A * | 3/1970 | Newfield .................. 73/150 R |
| 4,347,737 | A * | 9/1982 | Beach ......................... 73/159 |
| 4,698,507 | A * | 10/1987 | Tator et al. ................. 250/429 |
| 4,807,247 | A | 2/1989 | Robbins, III |
| 4,817,447 | A | 4/1989 | Kashima et al. |
| 4,957,012 | A * | 9/1990 | Cuddihy et al. ............... 73/866 |
| 4,995,273 | A | 2/1991 | Kisima et al. |
| 5,646,358 | A * | 7/1997 | Tikhtman et al. .......... 73/865.6 |
| 5,854,433 | A * | 12/1998 | Patel et al. ................. 73/865.6 |
| 5,898,816 | A * | 4/1999 | Heeger et al. ............... 392/408 |
| 5,980,103 | A | 11/1999 | Ikuno et al. |
| 6,073,500 | A | 6/2000 | Jorgensen et al. |
| 6,271,024 | B1 * | 8/2001 | Sve et al. ................. 435/303.1 |
| 6,331,683 | B1 | 12/2001 | Spannagel et al. |
| 6,533,452 | B1 * | 3/2003 | Hardcastle, III ............. 374/57 |
| 6,659,638 | B1 * | 12/2003 | Hardcastel, III ............. 374/57 |
| 6,703,592 | B2 | 3/2004 | Van Bilsen |
| 7,038,196 | B2 * | 5/2006 | Scott et al. ............... 250/252.1 |
| 7,174,781 | B2 * | 2/2007 | Webb ....................... 73/170.16 |
| 2002/0139928 | A1 | 10/2002 | Rathod |
| 2004/0178367 | A1 * | 9/2004 | Fischer et al. ........... 250/504 R |
| 2004/0211771 | A1 * | 10/2004 | Crandell ...................... 219/544 |
| 2005/0042759 | A1 * | 2/2005 | Boisseau et al. ............... 436/5 |
| 2005/0120811 | A1 * | 6/2005 | Hardcastle, III ........... 73/865.6 |
| 2005/0121605 | A1 * | 6/2005 | Rathod et al. ........... 250/252.1 |
| 2005/0167580 | A1 * | 8/2005 | Scott et al. ............... 250/252.1 |
| 2007/0034026 | A1 * | 2/2007 | Maciver et al. ............ 73/865.6 |
| 2007/0177144 | A1 * | 8/2007 | Hasegawa et al. .......... 356/328 |

* cited by examiner

*Primary Examiner*—Gail Verbitsky
(74) *Attorney, Agent, or Firm*—Vedder, Price, Kaufmann & Kammholz, P.C.

(57) ABSTRACT

An accelerated weathering test apparatus of the type used to concentrate solar radiation upon test specimens including a heating element that transfers energy to the test specimens. A temperature sensor is operatively coupled to one of the test specimens for generating a test signal representative of the operating temperature of the test specimens. A controller for generating a temperature set point is connected to the temperature sensor and responsive to the test signal for selectively controlling a power level applied to the heating element in order to control a rate at which energy is transferred to the test specimens.

19 Claims, 5 Drawing Sheets

SPECIMEN HEATER AND CONTROL SYSTEM FOR ACCELERATED WEATHERING TEST APPARATUS

The present disclosure is directed to an accelerated weathering test apparatus of the type used to concentrate solar radiation on test specimens, and more particularly, to an accelerated weathering test apparatus with a heating element and a temperature sensor operatively coupled with a test specimen to facilitate control of the test specimen operating temperature.

Manufacturers of exterior coatings, such as paints and finishes, as well as plastics and other components which tend to degrade under exposure to solar radiation and other weathering effects, often want to know how such products will perform following years of exposure. However, such manufacturers typically require such information in a much shorter time than it would take to expose such materials to weathering effects under normal conditions. Accordingly, accelerated weathering test devices have been developed which accelerate the effects of weathering due to outdoor exposure in a much shorter time so that manufacturers need not actually wait five or ten years in order to determine how their products will hold up after five or ten years of actual outdoor exposure.

One known accelerated weathering test device is disclosed in U.S. Pat. No. 2,945,417, issued to Caryl et al. The aforementioned test device includes a Fresnel-reflecting solar concentrator having a series of ten flat mirrors which focus natural sunlight onto a series of test specimens secured to a target board measuring approximately five (5) inches wide by fifty-five (55) inches long. The Fresnel-reflecting solar concentrator directs solar radiation onto the target board area with an intensity of approximately eight suns. Both the bed which supports the mirrors of the solar concentrator, and the target board, are supported by a frame which can be rotated to follow daily movements of the sun.

A solar tracking mechanism responsive to the position of the sun, controls the operation of an electric motor that is used to rotate the test apparatus to follow movements of the sun. The axis of rotation of the test machine is oriented in a north-south direction, with the north elevation having altitude adjustment capability to account for variation in the sun's altitude at various times during the year.

Such known testing devices are also provided with an air tunnel mounted above the target board. An air deflector causes air escaping from the air tunnel to be circulated across the test specimens mounted to the target board to prevent the test specimens from overheating due to the concentrated solar radiation to which they are exposed. The amount of air is controlled by the dimension of the gap between the deflector and the specimen. A squirrel cage blower communicates with the air tunnel for blowing cooling ambient air there through. In addition, water spray nozzles are provided proximate to target board for wetting the test samples at periodic intervals to simulate the weathering effects of humidity, dew, rain, etc.

Another known accelerated weathering test device is disclosed in U.S. Pat. No. 4,807,247 issued to Robins. The aforementioned test device includes all the structure previously described above with respect to the '417 patent and further includes a system for maintaining a uniform, constant test specimen temperature during daylight hours despite variations in ambient air temperature and variations in solar radiation intensity.

The system includes a temperature sensor mounted to the target board for exposure to the concentrated solar radiation and for generating an electrical signal indicative of the temperature of the test specimen mounted to the target board. The system further includes a control mechanism electrically coupled to the temperature sensor and responsive to the electrical signal generated thereby for selectively controlling the application of electrical power to the electrical motor included within the air circulation system. In this manner, the control mechanism serves to vary the speed of the electric motor and thereby control the flow rate of cooling ambient air circulating across the target board so that the temperature of the test specimen remains constant at the desired set point.

When the sensed temperature of the temperature sensor increases, the control mechanism increases the speed of the blower motor to circulate more ambient cooling air across the target board in an attempt to lower the temperature of the test samples in the direction of the desired set point. Similarly, if the sensed temperature of the temperature sensor drops below the desired nominal temperature, the control mechanism decreases the speed of the blower to permit the test samples to warm up back to the desired set point.

The temperature control mechanism also includes a user operable adjustment mechanism, in the form of the control knob, for allowing a user to set a static, desired sensor temperature. A bypass switch is also provided for allowing the user to operate the test device in the controlled temperature-mode as described above, or in an uncontrolled mode wherein the blower motor operates at a constant speed.

Standardized testing methods have been developed for operating accelerated weathering test devices of the type described above. The American Society for Testing and Materials (ASTM) has issued standards G90, E838, D4141, D3105, D3841, D5105, E1596 and D4364 covering the testing procedures and the operating parameters for conducting such outdoor accelerated weathering tests. Other standards and appraisals have also been developed and specified by the Society of Automotive Engineers (SAE), Ford, International Standards Organization (ISO), American National Standards Institute (ANSI), Japan Industrial Standard (JIS), namely, SAE J576, SAE J1961, Ford EJB-M1J14-A, Ford EST-M5P11-A, ISO 877, ANSI/NSF 54, JIS Z 2381 and MIL-T-22085D.

Apart from outdoor accelerated weathering test devices of the type described above, other test devices are also known which utilize an artificial source of radiation to expose the test specimens. An example of such a test device is disclosed in U.S. Pat. No. 3,664,188 issued to Kockott. While such test devices have the advantage of permitting precise control over radiation intensity, temperature and humidity, such test devices have often failed to duplicate the actual light spectrum of natural sunlight to which the specimens under test will actually be exposed in everyday use. It has been acknowledged and recognized by those of skill in the art that natural sunlight and artificial sunlight test apparatus are distinct from one another and provide different sets of empirical data.

Outdoor accelerated weathering test devices of the type described above in regard to U.S. Pat. Nos. 2,945,417 and 4,807,247, have the advantage of using natural sunlight, and hence the specimens under test are exposed to the actual spectrum of sunlight. However, disadvantages of outdoor accelerated weathering test devices have been discovered.

One disadvantage of outdoor weathering devices is the difficulty in maintaining the temperature of a test specimen within a temperature range while the specimen is exposed to outdoor conditions. For example, during hot testing periods, the test specimen may have to be cooled so that a temperature thereof is maintained near a test temperature.

In contrast, during cooler testing periods, the test specimen may have to be heated so that a temperature thereof is maintained near a test temperature. Accordingly, some outdoor weathering test apparatuses include specimen heating components and control systems for controlling such specimen heating components. A temperature sensor is typically placed near the test specimen, the output of which is then provided to a control system, which controls a heater to heat the test specimen. In these outdoor weathering test apparatuses, however, the temperature sensor does not detect the actual temperature of the test specimen, but only the temperature of an object to which the test specimen is attached or the temperature on or near the heater. Accordingly, although a control system controls the output of the heater in response to the input it receives from the temperature sensor, the control system is not actually controlling the temperature of the test specimen because the output of the sensor may not be indicative of the actual temperature of the test specimen.

Therefore, there exists a need in the art for a specimen heater and its associated control system that provide control of the actual temperature of the test specimen.

BRIEF DESCRIPTION OF THE DRAWINGS

Certain embodiments are shown in the drawings. However, it is understood that the present disclosure is not limited to the arrangements and instrumentality shown in the attached drawings, wherein.

DETAILED DESCRIPTION

Figure 1:
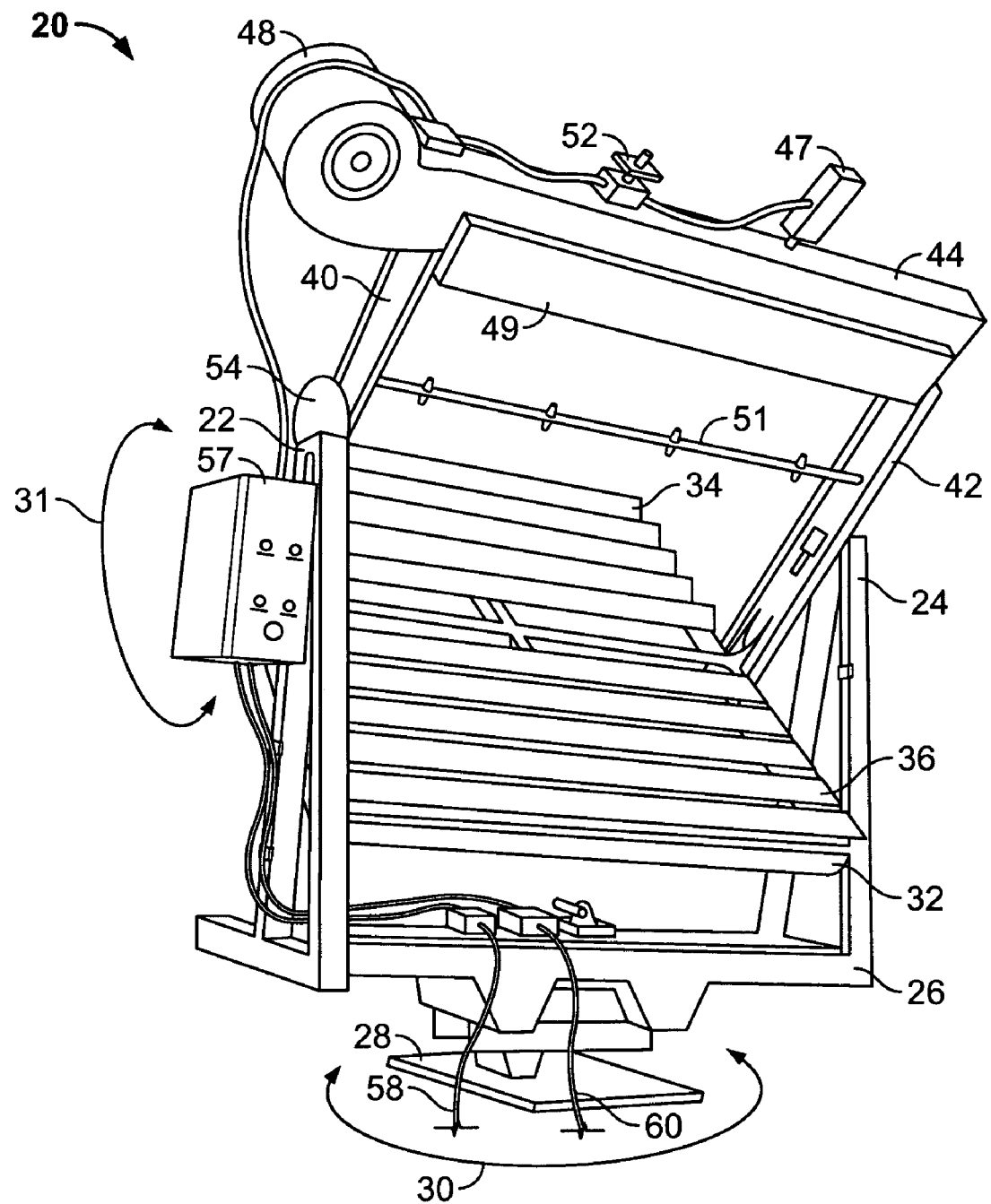
FIG. 1 illustrates a perspective view of a prior art weathering test apparatus.

For the purposes of promoting and understanding the principles disclosed herein, reference will now be made to the preferred embodiments illustrated in the drawings and specific language will be used to describe the same. It will nevertheless be understood that no limitation of the scope is thereby intended. Such alterations and further modifications in the illustrated device and such further applications are the principles disclosed as illustrated therein as being contemplated as would normally occur to one skilled in the art to which this disclosure relates.

In accordance with one principle aspect of the present disclosure, an accelerated weathering test apparatus of the type used to concentrate solar radiation upon test specimens includes a heating element that transfers energy to the test specimens. A temperature sensor is operatively coupled to at least one of the test specimens for generating a test signal representative of the operating temperature of the test specimens. A controller for generating a temperature set point is connected to the temperature sensor and responsive to the test signal for selectively controlling a power level applied to the heating element in order to control a rate at which energy is transferred to the test specimens.

Referring to FIG. 1, a prior art accelerated weathering test apparatus is designated generally by reference 20 and includes a pair of A-frame members 22 and 24 to support the operative portion of the apparatus. The lower ends of the A-frame members 22, 24 are interconnected by a base member 26 which is operatively connected to a ground member 28 in order to provide azimuth rotation in the direction indicated by arrow 30 and elevation rotation in the direction indicated by arrow 31. The elevation direction rotation accounts for periodic variation in the sun's altitude throughout the day.

Rotatively supported from the upper ends of A-frame members 22, 24 is a mirror bed frame 32 which supports a plurality of flat mirrors 34, 36. The plurality of mirrors 34, 36 are angled to reflect solar radiation directly impinging upon such mirrors to a target board 38 (see FIG. 2).

Figure 2:
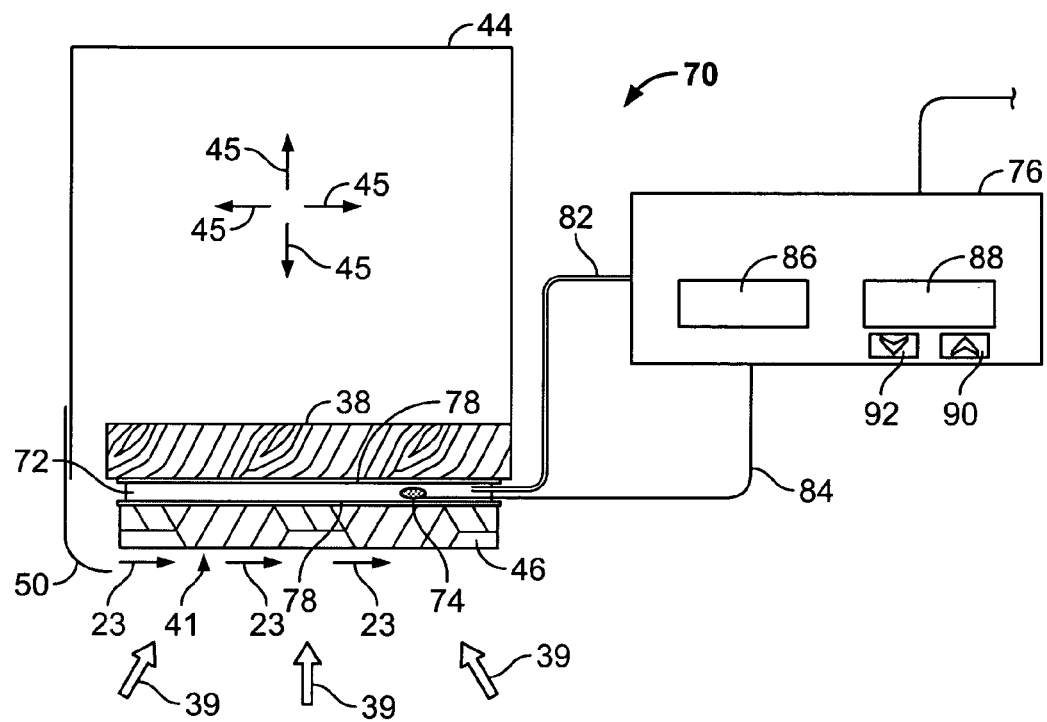
FIG. 2 illustrates a schematic diagram of a specimen heating system of the prior art weathering test apparatus of FIG. 1.

A pair of standards 40 and 42 extend outwardly from and perpendicular to mirror bed frame 32. An air tunnel 44 having a generally rectangular cross section is supported by the upper ends of standards 40, 42. Referring to FIG. 2, target board 38 is supported by the lower wall of air tunnel 44, and a plurality of test specimens 46 are mounted to the target board 38 for exposure to the concentrated solar radiation, represented in FIG. 2 by the upwardly extending arrows numbered 39. The target board 38 may include a single specimen 46 or a plurality of similar or different specimens 46. A squirrel cage blower assembly 48 communicates with one end of the air tunnel 44. Squirrel cage blower assembly 48 includes a fan driven by an electric motor to circulate cooling ambient air through air tunnel 44, represented in FIG. 2 by the outwardly extending arrows numbered 45. As shown in FIG. 2, air tunnel 44 includes a deflector 50 which extends for the length of target board 38 and causes cooling ambient air to be circulated across target board 38 for cooling test specimens 46, represented in FIG. 2 by the arrows numbered 23.

Standards 40, 42 are rotatively supported to upper ends of A-frame members 22, 24. A supporting shaft 43 (shown in FIG. 8) coincident with the axis of rotation in passing through standards 40, 42 rotably supports that portion of the test apparatus which tracks daily movements of the sun. In order to properly position the Fresnel-reflecting solar concentrator comprised by mirrors 34, 36 and reversible electric motor and related gear drive, generally designated by reference number 54, are provided for periodically rotating the mirror bed and target board assembly to track movements of the sun. The clutch preferably couples standard 40 to the shaft 43 (shown in FIG. 8) to rotate the mirror bed frame and target board assembly while permitting manual positioning of the unit at any time to correct for any positioning errors.

A solar cell tracking unit 52 controls the application of electrical power to a reversible motor in order to maintain the mirror bed frame 32 perpendicular to incident rays of sunlight. A solar tracker may be of the type which includes two balanced photo cells and a shadowing device mounted above such photo cells for shading them. When an imbalance is detected resulting from one photo cell receiving more sunlight than the other photo cell, an electrical error signal is generated which is amplified and used to apply power to the drive motor 54 for rotating the unit until the photo cells are again balanced, indicating that the unit is properly positioned with respect to the sun.

Also shown in FIG. 1 is a water spray nozzle assembly, designated generally by reference numeral 51. As shown in FIG. 1, spray nozzle assembly 51 is used to periodically spray water at the test specimens to simulate dew, rain, etc.

A hinge shield or cover 49 is shown coupled to the air tunnel 44 opposite the air deflector 50. A door release mechanism 47 is disposed on the air tunnel 44 for engaging and maintaining the shield in an open position. Upon release, the shield 49 assumes the closed position such that concentrated solar radiation reflected by the plurality of mirrors 35 does not reach the test specimens 46.

Secured to the target board 38 is a feedback device (not shown) having at least one temperature sensitive component secured in heat conductive relationship therewith. Such component may be a thermistor, thermocouple, resistance temperature device, integrated circuit temperature device, semiconductor temperature device, or any other suitable device for detecting temperature of the feedback device. The feedback device may be formed from a standardized material having known thermal conductive properties or may be formed from a material similar to that of the test specimen. The temperature sensitive component may be embedded within, attached to a back surface or attached to a front surface of the feedback device. Alternatively, a non-contact optical temperature sensing device, infrared sensor, radiation thermometer, pyrometric sensor, bimetallic sensor, filled system thermometer, liquid or gas, or thermal imaging system may be used in order to determine the temperature of the feedback device. The feedback device is preferably coated with black paint to insure that the feedback device will absorb solar radiation impinging upon the area of the target board 38 to which the feedback device is secured. An appropriate black paint which may be used for this purpose is DUPONT DULUX Super Black High Temperature Enamel.

Referring again to FIG. 1, a controller box 57 houses the power and controller systems for the apparatus 20. A power cable 58 supplies electrical power to the apparatus 20 for powering the electric motor 54, which also actuates the fan 48. A signal cable 60 is connected to the controller system disposed within the control box 57 for communication with remotely disposed devices, such as the feedback devices and input device, as will be discussed below or for communication with a central command for governing the operation of the apparatus 20 in accordance with the present invention.

Figure 3:
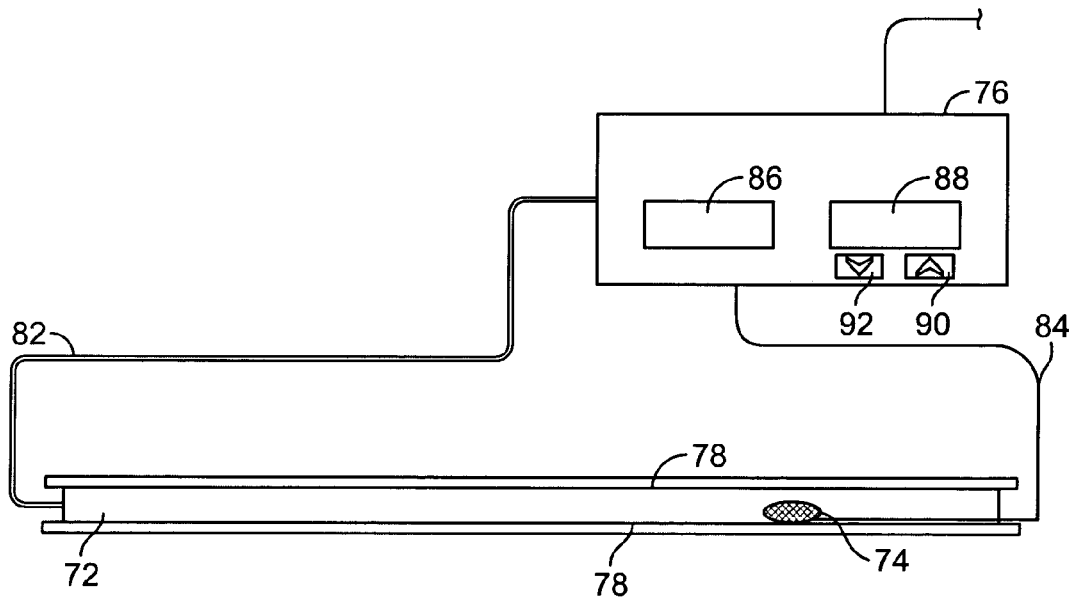
FIG. 3 illustrates a schematic diagram of portions of the specimen heating system of FIG. 2.

Referring to FIGS. 2 and 3, a schematic cross sectional diagram of a typical prior art specimen heating system 70 is shown. The specimen heating system 70 includes a heating element 72, a temperature sensor 74 embedded in the heating element 72, a platen and a controller 76. As shown in FIG. 3, the platen includes a pair of spaced apart plates 78 sandwiching the heating element 72. The plates 78 may be constructed from aluminum or any suitable metal. The heating element 72 may be a wire wound silicone rubber heater. However, any suitable heating element may be used between the plates 78. The heating element 72 receives power through the power cable 82 from the controller 76. Accordingly, as will be described in the following, the controller 76 can control the heating output of the heating element 72 by supplying the necessary power to the heating element 72 through the heating element power cable 82. The temperature sensor 74 is disposed between the plates 78. The temperature sensor 74 provides an output signal that is indicative of the temperature near the temperature sensor 74. The test signal is conveyed to the controller 76 through the test signal cable 84.

Figure 4:
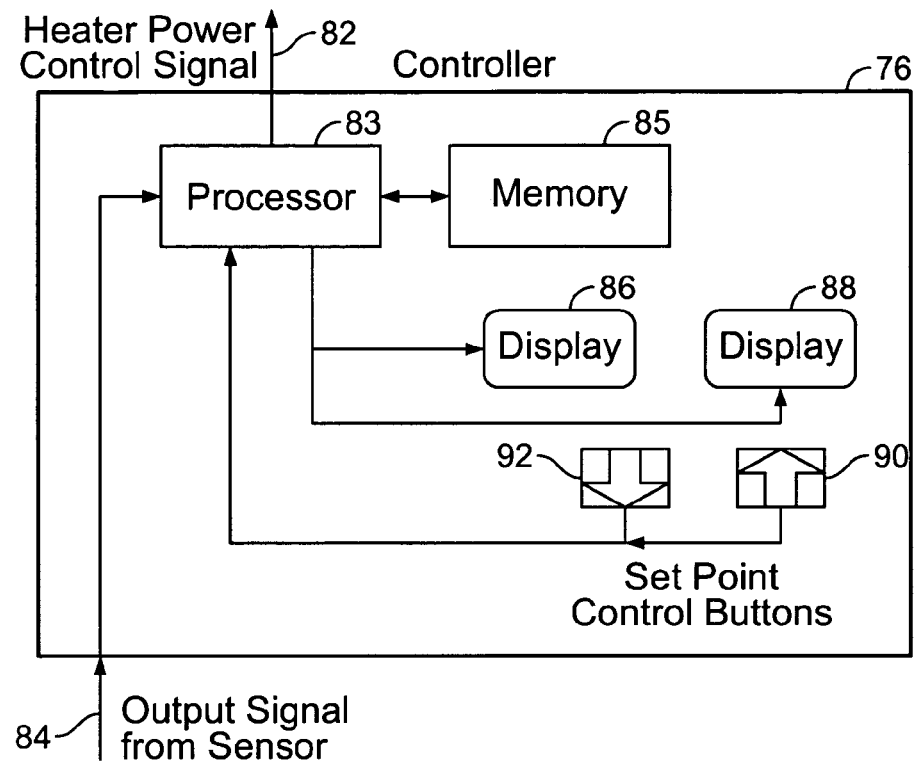
FIG. 4 illustrates a schematic diagram of a controller for the specimen heating system of FIG. 2.

Referring also to FIG. 4, the controller 76 may include a processing unit 83 and memory 85 that stores programming instructions pertaining to the control of an actual temperature of the temperature sensor 74 or heating element relative to a set point temperature entered by an operator. The controller may also include an analog control circuit for providing the following functionality. The controller 76 receives the test signal from the temperature sensor 74 and displays the temperature conveyed by the test signal on an actual temperature display 86. The controller 76 also includes a set point display 88, which shows the set point temperature. A first set point control button 90 may be disposed near the set point display 88, and a second set point control button 92 may also be disposed near the set point display 88. The first and second set point control buttons 90 and 92, allow the operator to increase or decrease the set point temperature displayed on the set point display 88. For example, as shown in FIGS. 2-4, the first set point control button 90 can increase the set point temperature, while the second point control button 92 can decrease the set point temperature. If the temperature that is displayed on the actual temperature display 86 is not equal or near the set point temperature that is displayed on the set point display 88, the controller 76 will either increase or decrease the power to the heating element 72 to increase or decrease, respectively, the temperature sensed by the temperature sensor 74. Accordingly, the controller 76 adjusts the temperature near the temperature sensor 74 to match or nearly match the set point temperature.

As shown in FIG. 2, the heating element 72 is attached to the outside of the target board 38 between the specimen 46 and the target board 38. Because the temperature sensor 74 is disposed between the plates 78 and is near or in contact with the heating element 72, the temperature that is sensed by the temperature sensor 74 may not reflect the actual temperature of the specimen 46. In particular, the exposure surface 41 of the specimen 46 may be at a highly different temperature than the temperature that is sensed by the temperature sensor 74. Accordingly, although the controller 76 controls the actual temperature sensed near the sensor 74, the sensed temperature may not reflect the temperature that is experienced by the specimen 46.

Figure 5:
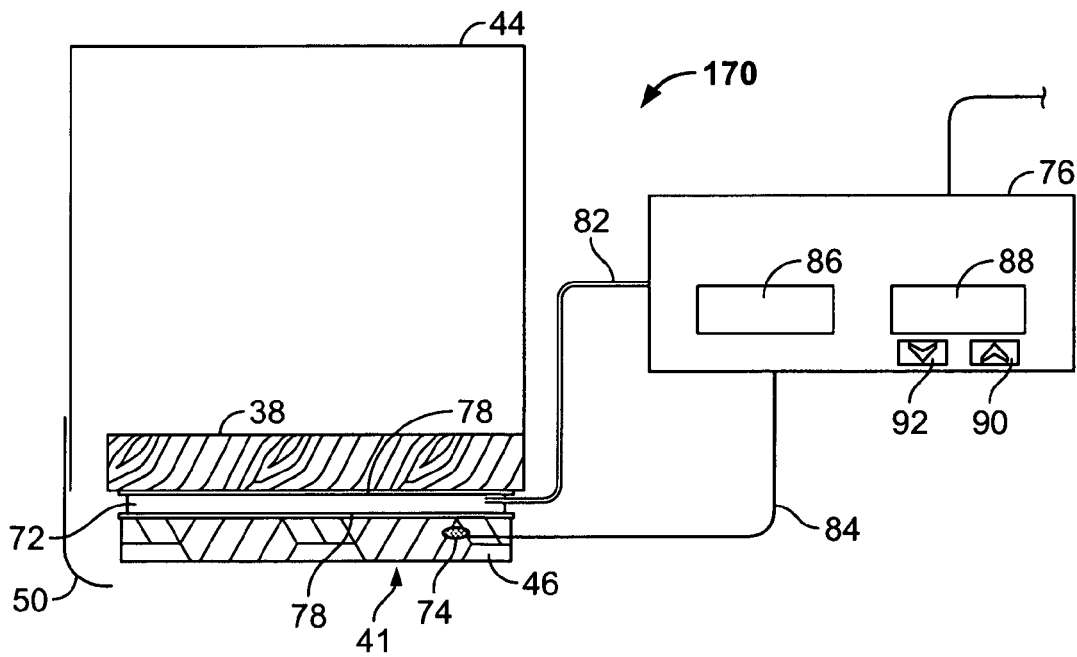
FIG. 5 illustrates a schematic diagram of an embodiment of a specimen heating system constructed in accordance with the teachings the present disclosure.

Referring to FIG. 5, a schematic cross sectional diagram of one embodiment of a specimen heating system 170 constructed in accordance with the teachings of the present disclosure is shown. The specimen heating system of FIG. 5 is similar to the specimen heating system 70 in all respects, except that, in the specimen heating system 170, the temperature sensor 74 is embedded in the test specimen 46. Accordingly, the temperature sensor 74 can sense the temperature inside the test specimen 46 and the regions of the test specimen 46 that surround the temperature sensor 74. The noted regions may also include the internal side of the test specimen 46 that is attached to the heating platen 72 and the exposure surface 41 of the test specimen 46. Therefore, the actual temperature display 86 may represent a temperature that more accurately reflects the actual temperature of the test specimen 46. The temperature sensor 74 may be configured as a thermistor, thermocouple, resistance temperature device, integrated circuit temperature device, semiconductor temperature device, a non-contact optical temperature sensing device, infrared sensor, radiation thermometer, pyrometric sensor, bimetallic sensor, filled system thermometer, liquid or gas, thermal imaging system, or any other suitable temperature detection device.

If the temperature of the test specimen 46 is uniform throughout the test specimen 46, the temperature sensed by the temperature sensor 74 reflects the temperature of the entire test specimen 46. However, if the temperatures throughout the test specimen 46 vary locally, the temperature sensed by the temperature sensor 74 will be a local temperature, which may be the temperature of the test specimen near or surrounding the temperature sensor 74. However, since the heating element 72 and plates 78 may cover the entire width of the test specimen 46, the temperature variations inside the test specimen 46 may be small. Therefore, the temperature sensed by the temperature sensor 74 may generally reflect the temperature of the test specimen 46. To provide for local temperature sensing at various points inside or on the surface of the specimen 46, the temperature sensor 74 can be placed anywhere on or in this test specimen 46.

Figure 6:
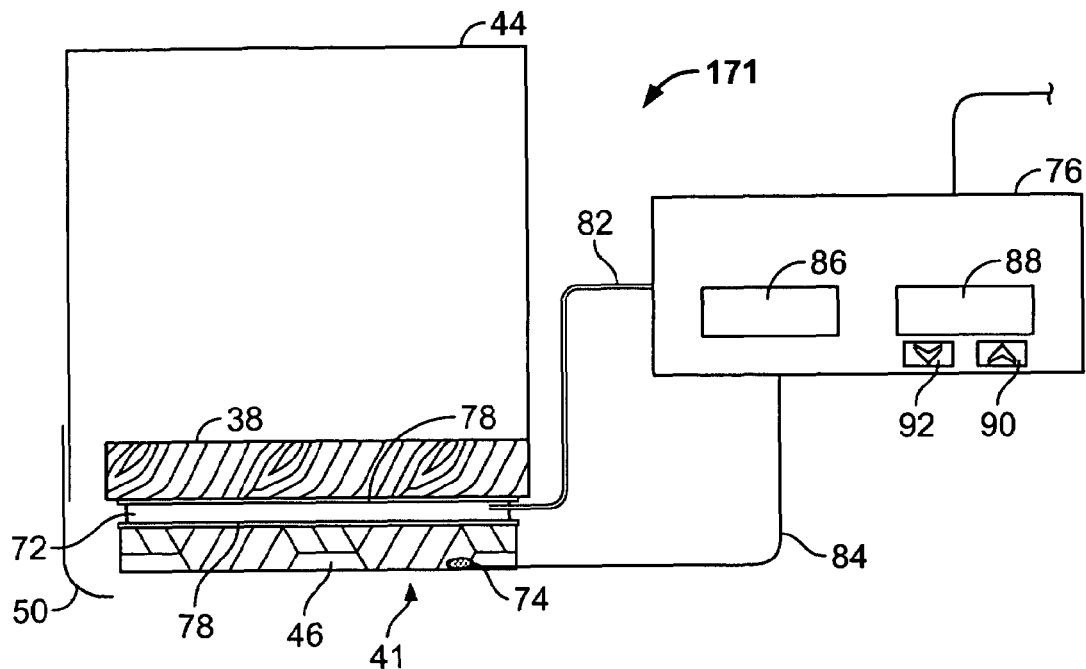
FIG. 6 illustrates a schematic diagram of another embodiment of a specimen heating system constructed in accordance with the teachings the present disclosure.

Referring to FIG. 6, a schematic diagram of another embodiment of the specimen heating system 171 of the present disclosure is shown. The specimen heating system of FIG. 6 is similar to the specimen heating system 70 in all respects, except that, in the specimen heating system 171, the temperature sensor 74 is disposed near or on the exposure surface 41 of the test specimen 46. Accordingly, the temperature experienced by the temperature sensor 74 may likely reflect the temperature of the test specimen 46 at the exposure surface 41 or inside the test specimen 46 near the exposure surface 41. Accordingly, when the controller 76 is controlling the temperature that is experienced by the temperature sensor 74, the controller 76 may be actually controlling the temperature of the test specimens 46 at or near the exposure surface 41.

Figure 7:
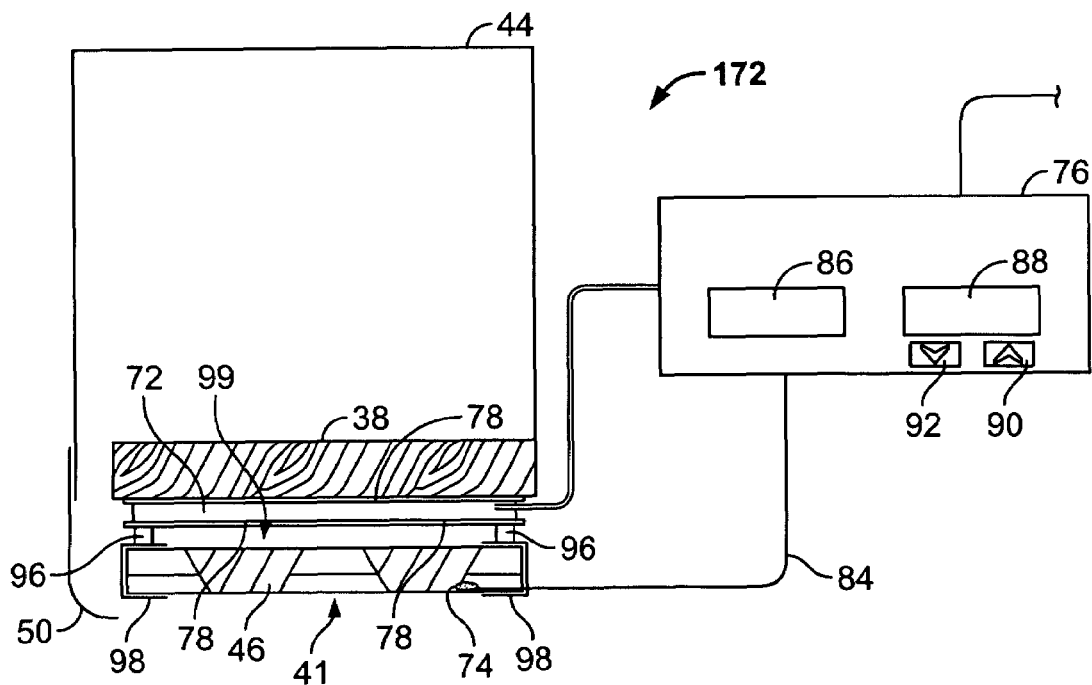
FIG. 7 illustrates a schematic diagram of another embodiment of a specimen heating system constructed in accordance with the teachings the present disclosure.

Referring to FIG. 7, a schematic cross sectional diagram of another embodiment of specimen heating system 172 constructed in accordance with the teachings of the present disclosure is shown. The specimen heating system of FIG. 7 is similar to the specimen heating systems 170 and 171 in all respects, except that, in the specimen heating system 172, the test specimen 46 does not contact the heating element 72 or platen 78. The specimen heating system 172 includes a pair of standoffs 96, to which a specimen frame 98 is attached. Accordingly, the standoffs 96 provide an air gap 99 between the specimen frame 98 and the heating element 72 or platen 78. The specimen frame 98 is configured to hold the test specimen 46. The air gap 99 between the test specimen 46 and the heating element 72 or platen 78 allows air to flow through the gap 99 and cool the specimen 46. When heating of the specimen 46 is necessary, the heating element 72 or platen 78 can generate heat, which may be transferred to the test specimen 46 through the air gap 99. Therefore, the test specimen 46 can be cooled when necessary through the air gap 99, and can be heated when necessary by the heating element 72 or platen 78.

In certain testing situations, it may not be necessary to heat the test specimen 46, because the solar radiation may be sufficient during the day to keep the test specimen 46 at the set point temperature. Furthermore, during testing periods when the solar radiation is intense, the test specimen 46 may actually have to be cooled so that the temperature of the test specimen 46 remains at or near the set point temperature. Therefore, during certain testing situations, it may be necessary to cool the test specimen during the day and heat the test specimen at night. The specimen heating system 172 provides cooling of the test specimen 46 by providing the air gap 99. When the heating element 72 is turned off, air flowing through the air gap 99 can cool the test specimen 46.

Figure 8:
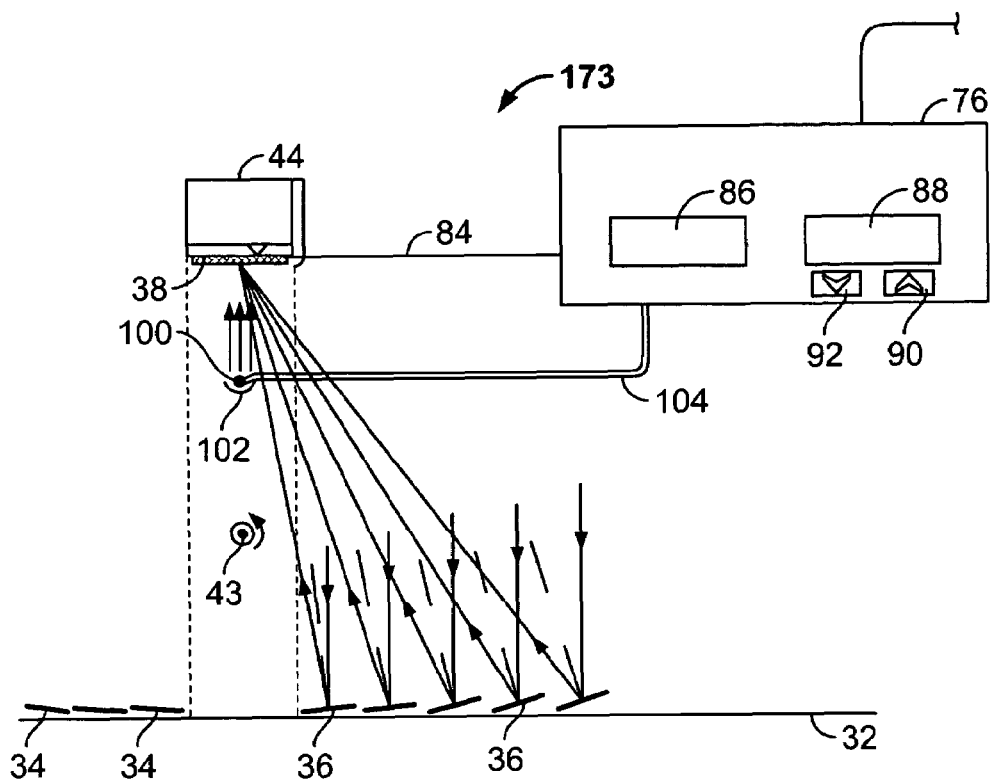
FIG. 8 illustrates a schematic diagram of another embodiment of a specimen heating system constructed in accordance with the teachings the present disclosure.

In FIGS. 5-7, the heating element 72 may be disposed between the target board 38 and the test specimen 46. Furthermore, the heating element 72 of FIGS. 5 and 6 directly contacts the test specimen 46. However, the test specimen 46 may be heated by a heating element that is not near or in contact with the test specimen 46. Referring to FIG. 8, a schematic diagram of another embodiment of a specimen heating system 173 constructed in accordance with the teachings of the present disclosure is shown. The specimen heating system 173 of FIG. 8 includes a heating element 100 that may be disposed between the mirror bed frame 32 and the specimen 46 and does not contact the specimen 46. The heating element 100 directs heat toward the test specimen 46. The heating element 100 may also include a reflector 102 that reflects the heat from the heating element 100 up toward the test specimen 46. The controller 76 controls the power delivered to the heating element 100 by the heating element power cable 104. Accordingly, the controller 76 can keep the temperature that is experienced by the temperature sensor 74 of the test specimen 46 (not shown) at or near the set point temperature.

Figure 9:
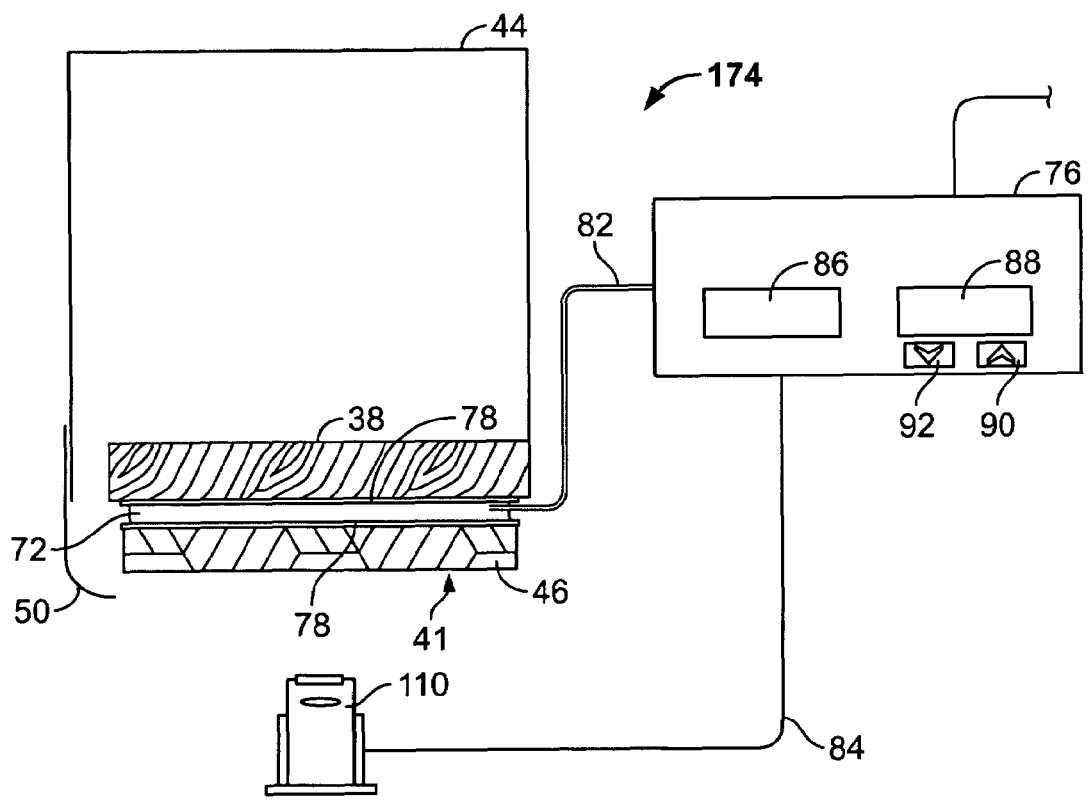
FIG. 9 illustrates a schematic diagram of another embodiment of a specimen heating system constructed in accordance with the teachings the present disclosure.

The temperature sensor 74 that is used to sense the temperature of the test specimen 46 may also be a non-contact temperature sensor or an external temperature sensor. Referring to FIG. 9, a schematic cross sectional diagram of another embodiment of the specimen heating system 174 constructed in accordance with the teachings of the present disclosure is shown. The specimen heating system 174 includes a non-contact temperature sensor 110 that is disposed outside the test specimen 46. The temperature sensor 110 may be any one of the known optical temperature sensors that are typically used to sense the temperature of a distant object. For example, the non-contact temperature sensor 110 can be an optical pyrometer that views the exposure surface 41 of the test specimen 46. However, any suitable non-contact temperature sensor may be used outside the test specimen 46 to sense the temperature of the test specimen 46 during testing.

The disclosed specimen heating systems 170-174 are not limited to the particular respective embodiments shown in the foregoing. For example, the temperature sensors 74 of FIGS. 5 and 7 may be replaced with a non-contact temperature sensor 110 shown in FIG. 9 and implemented as illustrated in FIG. 9 of the specimen heating system 170. In another example, the heating element 72 of FIGS. 5-7 can be replaced with the heating element 100 and the reflector 102 of FIG. 8. Accordingly, one of ordinary skill in the art will readily appreciate that any combination of the above-described embodiments for the specimen heating system 170-174 are possible to achieve a desired testing result.

Furthermore, while the particular preferred embodiments have been shown and described, it will be obvious to those skilled in the art that changes and modifications may be made without departing from the teaching of the disclosure. The matter set forth in the foregoing description and accompanying drawings is offered by way of illustration only and not as limitation. The actual scope of the disclosure is intended to be defined in the following claims when viewed in their proper perspective based on the related art.

What is claimed is:

1. An accelerated weathering test apparatus of the type used to concentrate solar radiation upon test specimens operatively coupled to a target board, including a reflecting solar concentrator operatively coupled and disposed in opposition to the target board and adapted for adjusting an operating temperature of the test specimens, the accelerated weathering test apparatus comprising:
   a heating element that transfers energy to the test specimens, the heating element operatively coupled to the apparatus;
   a temperature sensor contiguous to at least one of the test specimens for generating a test signal representative of the operating temperature of the test specimens; and
   a controller for generating a temperature set point connected to the temperature sensor and responsive to the test signal for selectively controlling a power level applied to the heating element in order to control a rate at which energy is transferred to the test specimens, the rate being generally decreased when the operating temperature of the test specimens is greater than the temperature set point, and the rate being generally increased when the operating temperature of the test specimens is less than the temperature set point, and the rate being generally maintained constant when the operating temperature of the test specimens is substantially equal to the temperature set point.

2. The apparatus as recited in claim 1, wherein the heating element is a platen disposed contiguous with the target board and the test specimens.

3. The apparatus as recited in claim 2, wherein the platen includes a pair of aluminum plates disposed on opposing sides of a wire wound silicone rubber heating device.

4. The apparatus as recited in claim 1, wherein the heating element is a platen disposed contiguous with the target board and spaced from the test specimens.

5. The apparatus as recited in claim 4, wherein the platen includes a pair of aluminum plates disposed on opposing sides of a wire wound silicone rubber heating device.

6. An accelerated weathering test apparatus of the type used to concentrate solar radiation upon test specimens operatively coupled to a target board, including a reflecting solar concentrator operatively coupled and disposed in opposition to the target board and adapted for adjusting an operating temperature of the test specimens, the accelerated weathering test apparatus comprising:
   a heating element that transfers solar energy to the test specimens, the heating element operatively coupled to the apparatus;
   a temperature sensor operatively coupled to at least one of the test specimens for generating a test signal representative of the operating temperature of the test specimens; and
   a controller for generating a temperature set point connected to the temperature sensor and responsive to the test signal for selectively controlling a power level applied to the heating element in order to control a rate at which solar energy is transferred to the test specimens, the rate being generally decreased when the operating temperature of the test specimens is greater than the temperature set point, and the rate being generally increased when the operating temperature of the test specimens is less than the temperature set point, and the rate being generally maintained constant when the operating temperature of the test specimens is substantially equal to the temperature set point;
   wherein the heating element is a platen disposed contiguous with the target board and spaced from the test specimens; and
   wherein standoffs separate the platen from the test specimens to define an air gap.

7. The apparatus as recited in claim 1, wherein the heating element is an infra red device for emitting energy incident on an exposure surface of the test specimens.

8. The apparatus as recited in claim 7, wherein the infra red device is disposed at a spaced location from the test specimens.

9. The apparatus as recited in claim 7, wherein the infra red device further includes a reflector directed at the test specimens.

10. The apparatus as recited in claim 1, wherein the temperature sensor may be selected from the group consisting of a thermistor, thermocouple, resistance temperature device, integrated circuit temperature device, semiconductor temperature device, bi-metallic sensor, filled system thermometer, liquid or gas.

11. The apparatus as recited in claim 10, wherein the temperature sensor is embedded within one of the test specimens.

12. The apparatus as recited in claim 10, wherein the temperature sensor is disposed on an exposure surface of one of the test specimens.

13. The apparatus as recited in claim 1, wherein the temperature sensor is a non-contact device for monitoring an exposure surface of the test specimens.

14. The apparatus as recited in claim 13, wherein the non-contact device may be selected from a group consisting of an optical pyrometer, infrared sensor, radiation thermometer, pyrometric sensor, or thermal imaging system.

15. The apparatus as recited in claim 1, wherein the controller includes a processing unit and memory that stores programming instructions that, when used by the processing unit, causes the controller to function to: monitor the generated temperature set point, apply the power level to the heating element relative to the temperature set point, determine the operating temperature of the test specimen from the test signal, compare the operating temperature to the temperature set point, adjust the power level to the heating element, and repeat the above steps at pre-selected intervals for a desired period of time.

16. The apparatus as recited in claim 1, wherein the temperature set point is generated by an input to the controller.

17. The apparatus as recited in claim 16, wherein the input is a signal from a temperature sensitive component, an apparatus for replaying a recorded environment temperature cycle, an apparatus for generating a static set point or an apparatus for generating a complex temperature cycle.

18. The apparatus as recited in claim 1, wherein the controller determines the power level for transferring energy based upon the heating element, the temperature set point and the test specimens.

19. The apparatus as recited in claim 1, wherein the controller compares the operating temperature of the test specimens and the temperature set point to adjust the power level and repeats the above steps at pre-selected intervals for a desired period of time.

* * * * *